United States Patent [19]
Leroy et al.

[11] Patent Number: 5,466,241
[45] Date of Patent: Nov. 14, 1995

[54] LIGATURE AND/OR SUTURE SYSTEM FOR ENDOSCOPIC SURGERY

[76] Inventors: Joël Leroy, Boulevard Lamendin, 62160 Bully les Mines; Gilles Catteau, 1 Rue Charles Chamberland, 28630 Barjouville, both of France

[21] Appl. No.: 230,668

[22] Filed: Apr. 21, 1994

[30] Foreign Application Priority Data

Apr. 23, 1993 [FR] France ................................ 93 04839

[51] Int. Cl.⁶ .................................................. A61B 17/00
[52] U.S. Cl. ........................... 606/139; 606/144; 606/148
[58] Field of Search ................................. 606/139, 144, 606/148, 151

[56] References Cited

U.S. PATENT DOCUMENTS

| | | |
|---|---|---|
| 2,610,631 | 9/1952 | Calicchio . |
| 3,476,115 | 11/1969 | Graeff et al. .............................. 606/139 |
| 4,235,238 | 11/1980 | Ogiu et al. . |
| 5,041,129 | 8/1991 | Hayhurst et al. ..................... 606/139 X |
| 5,100,417 | 3/1992 | Cerier et al. ............................. 606/139 |
| 5,201,744 | 4/1993 | Jones . |
| 5,281,238 | 1/1994 | Chin et al. ........................... 606/139 X |
| 5,330,491 | 7/1994 | Walker et al. ........................ 606/139 X |
| 5,334,199 | 8/1994 | Yoon .................................... 606/139 X |

FOREIGN PATENT DOCUMENTS

| | | |
|---|---|---|
| 3504202 | 8/1985 | European Pat. Off. . |
| 0477020 | 3/1992 | European Pat. Off. . |
| 736756 | 11/1932 | France . |
| 9204296 | 6/1992 | Germany . |
| 975006 | 11/1982 | U.S.S.R. ............................... 606/139 |
| 1251885 | 4/1987 | U.S.S.R. . |
| 92/11810 | 7/1992 | WIPO . |

Primary Examiner—Stephen C. Pellegrino
Assistant Examiner—Michael Peffley
Attorney, Agent, or Firm—Paul A. Coletti

[57] ABSTRACT

A ligature and/or suture system for endoscopic surgery, comprising, in combination: a tie for ligature or for suture, slidably mounted in the longitudinal channel of a separate tubular endpiece; and a rigid support including a handle secured to an elongate rod which is provided at its proximal end remote from the handle with a reception cradle suitable for removably receiving the tubular endpiece, and with a through lateral window whereby said cradle opens out to the outside of the support to enable the tie to pass therethrough such that traction exerted on the distal end of the tie relative to the support serves to tighten the ligature or the suture.

21 Claims, 8 Drawing Sheets

FIG_10

FIG_11

FIG_12

# LIGATURE AND/OR SUTURE SYSTEM FOR ENDOSCOPIC SURGERY

The present invention relates to the field of instruments for endoscopic surgery.

BACKGROUND OF THE INVENTION

The present invention relates more particularly to instruments for endoscopic surgery that are adapted to ligate or suture an organ.

Endoscopic surgery covers any operation performed by inserting instruments into the organism via natural orifices or via miniscule incisions, with examination inside the body taking place by means of an optical instrument inserted into the organism by the same means.

It is known that endoscopic surgery provides numerous advantages over conventional surgical techniques in which the surgeon operates by opening the body.

The following advantages may be mentioned in particular:

- endoscopic surgery avoids scars;
- it is more comfortable for the patient and gives rise to less pain;
- it leads to lower consumption of auxiliary medication, in particular analgesics and pain killers;
- it enables scarring to take place more quickly; and
- it makes quicker discharge possible with consequent shorter stays in hospital, in particular because of the disappearance of the operative and post-operative complications associated with opening the body as is done in conventional techniques.

Under such conditions, it is now believed that within the next 10 years, ¾ of gynecological operations and of operations associated with the digestive system will be performed by endoscopic surgery.

Numerous miniaturized instruments have been proposed for that purpose, and in particular forceps, scissors, paddles, electric scalpels, . . . . All such miniaturized instruments are designed to be inserted into the body by means of small-section trocars.

In the particular field of ligatures or sutures for endoscopic surgery, surgeons have various techniques available to them.

These are described, for example, in the document: British Medical Bulletin (1986), Vol. 42, No. 3, pp. 284–295 "Operative pelviscopy", K. Semm.

The first technique referred to as "loop ligature" uses a filament provided at its end with a loop or lasso having a slip knot. To use that ligature, the loop is inserted into the body cavity by means of a trocar and it is engaged on the organ to be ligated, after which it is tightened thereon. The loop can be tightened by means of a knot-pusher instrument.

This can be done by using various instruments that include a rectilinear rod adapted to be engaged in the trocar and including at its proximal end a groove or fork whereby the knot-pusher is engaged on the filament and serves to push against the slip knot so as to tighten the loop during relative displacement between the knot-pusher and the filament. Examples of such conventional grooved or forked knot-pushers are described in the following documents: 1) Obstetrics & Gynecology, Vol. 78, No. 1, July 1991, "A new clinch knot", Peter V. Weston, and 2) Obstetrics & Gynecology, Vol. 79, No. 1, January 1992, "A simple method for ligating with straight and curved needled in operative laparoscopy", Harry Reich et al.

Knot-pushers with a lateral groove or fork suffer from a major drawback: they cause the filament and the loop to twist about their axis; this is because it is necessary, in order to keep the knot in the groove or the fork, to ensure that the filament passes around the axis of the knot-pusher. This phenomenon of the loop twisting increases as the loop is tightened and can therefore cause the loop to be tightened insufficiently.

Figure 1:
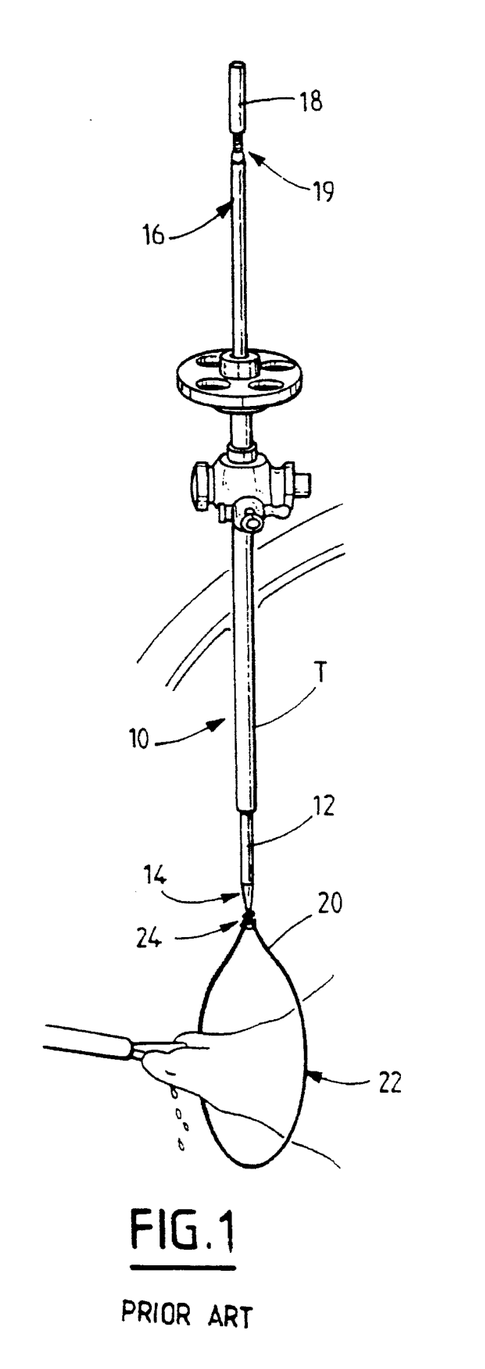
FIGS. 1 and 2 are described above and show a prior art system.
Figure 2:
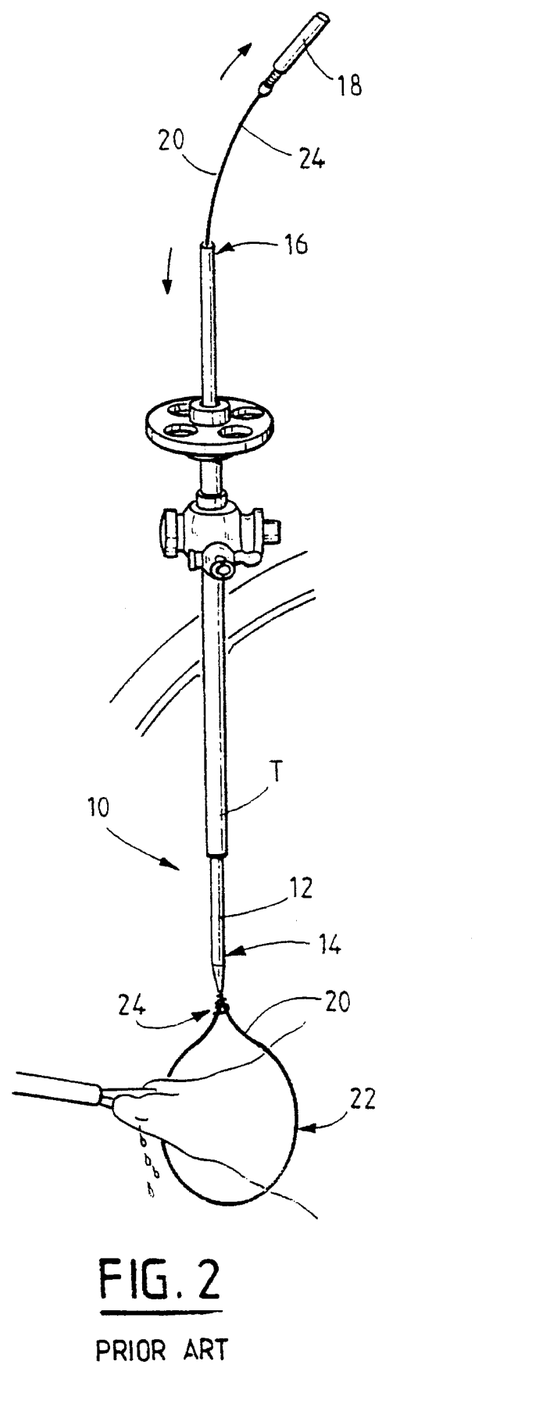

To facilitate the operation of ligating, proposals have also been made (as shown in accompanying FIGS. 1 and 2) for a knot-pusher 10 that comprises an elongate rectilinear sleeve 12 adapted to be engaged in a trocar T and that possesses a longitudinal channel in which the ligature filament 20 is engaged. The filament emerges at the proximal end 14 of the sleeve 12 in the form of a loop 22 having a slip knot 24. In addition, the sleeve 12 is provided at its distal end 16 with an endpiece 18 fixed on the distal end 24 of the filament 20. Initially, the endpiece 18 is connected to the sleeve 12 via a zone of weakness 19. To use this knot-pusher 10, once the loop 22 has been engaged on the organ to be ligated (as shown in FIG. 2), it suffices to separate the endpiece 18 from the sleeve 12 at the zone of weakness 19 and to move said members apart to tighten the loop 22.

A second technique consists in making the loop of the ligature around the organ during the operation. In that case, the slip knot may be made entirely within the body, by manipulating the filament inside the body cavity, or it may be made outside the body by extracting the strand of filament that has gone round the organ via the trocar, forming the slip knot outside the body, and then putting the knot back into the trocar and thus into the body cavity to tighten the ligature. In that case also, it is generally necessary to use a knot-pusher, at least when the knot is tied outside the body. For that purpose it is possible to use a conventional grooved or forked knot-pusher as mentioned above. Suture filaments mounted on knot-pushers with separable sleeves and endpieces of the type shown in FIGS. 1 and 2 are now also available to surgeons.

A third technique consists in using a suture filament, i.e. a filament provided with a needle, instead of a ligature filament. In that case also, the slip knot may be made inside the body or outside it. The suture may be tightened by means of a conventional forked or grooved knot-pusher. Suture filaments mounted on knot-pushers with separable sleeves and endpieces of the type shown in FIGS. 1 and 2 are also available to surgeons.

The various ligature and suture techniques recalled above are presently in use by surgeons.

However, those techniques do not give total satisfaction.

In particular, it is rather difficult to manipulate grooved or forked knot-pushers as described, for example, in the above-mentioned Obstetrics & Gynecology documents.

A drawback of knot-pushers having a separable sleeve and endpiece and of the type shown in accompanying FIGS. 1 and 2 is that they require bulky packaging adapted to the length of the sleeve. That drawback is particularly inconvenient in that the surgeon is often not in a position to decide on the kind of filament and its diameter, or on the type of needle that needs to be used for ligature or suture purposes until the last moment, thus requiring a full range of kits to be available in the operating theatre all having separable sleeve-and-endpiece knot-pushers fitted with ligature or suture filaments but of different diameters, of different natures, and with respect to the suture filaments, with needles of various shapes, such as rectilinear needles, ski-shaped needles, etc. . . . . That leads to a very considerable volume being required solely for ligatures and sutures. In addition, it should be observed that the sizes of the packages required for such separable sleeve-and-endpiece knot-pushers makes sterilization quite expensive.

OBJECTS AND SUMMARY OF THE INVENTION

An object of the present invention is to improve existing ligature and suture systems for endoscopic surgery.

A main object of the present invention is to reduce the volume of sterile packaging required for ligatures and/or sutures.

Another main object of the present invention is to make available a novel ligature or suture system enabling manipulation during surgery to be simplified.

According to the present invention, these objects are achieved by means of a system comprising:

a tie for ligature or for suture, slidably mounted in the longitudinal channel of a separate tubular endpiece; and a rigid support including a handle secured to an elongate rod which is provided at its proximal end remote from the handle with a reception cradle suitable for removably receiving the tubular endpiece, and with a through lateral window whereby said cradle opens out to the outside of the support to enable the tie to pass therethrough such that traction exerted on the distal end of the tie relative to the support serves to tighten the ligature or the suture.

As will be understood on reading the following description, the present invention makes it possible to package ties fitted with respective tubular endpieces individually in sterile packages but separately from supports therefor.

According to another advantageous characteristic of the present invention, the distal end of a tie is provided with a cursor and the handle of the support is provided with a complementary slider.

That characteristic makes it possible, in particular, to manipulate the system with one hand only.

The present invention also provides, separately, firstly ties fitted with respective tubular endpieces, and secondly corresponding supports including a handle and a support having a reception cradle.

Document DE-A-3 504 202 describes a surgical ligature kit comprising an elongate tubular applicator and a single-piece link device constituted by a clamping collar engaged in a snap-fastening head secured to said collar The means described in that document are far removed from those of the invention. Firstly, the means of document DE-A-3 504 202 are not adapted to endoscopic type intervention. Secondly, that document does not describe a tie for ligature or suture that is slidably mounted in the longitudinal channel of a separate tubular endpiece, as is the case in the present invention. This difference is fundamental: after the ligature or suture has been tightened, the invention makes it possible for it to be secured by means of a knot by using the tubular endpiece as a knot-pusher. In contrast, the link device described in document DE-A-3 504 202 does not enable such a locking knot to be implemented. Consequently, it requires the link device to have welding means and sectioning means available at the end of the applicator. Furthermore, because the presence of such welding means and sectioning means at the end of the applicator is essential, the applicator does not include a reception cradle for the head of the link device at its proximal end, but only comprises a reception chamber for said head, set back from said proximal end. Finally, as shown in FIG. 3 of that document, engagement of the free end of the tie in said head requires an additional looped filament. Such a filament is very difficult to use.

BRIEF DESCRIPTION OF THE DRAWINGS

Other characteristics, objects and advantages of the present invention appear on reading the following detailed description given with reference to the accompanying drawings given by way of non-limiting example, and in which:

FIG. 5bis is a view similar to FIG. 5, but showing a portion of the proximal end of the support in a lateral view orthogonal to FIG. 5;

FIG. 7bis is a perspective view showing a variant embodiment of a cursor in accordance with the present invention;

MORE DETAILED DESCRIPTION

As mentioned above, the system of the present invention comprises a combination of a tie 100 and of a support 200.

The tie 100 essentially comprises a filament 110 and a main endpiece 120 that is constituted by a piece which is distinct from the filament 110.

The filament may be made of any appropriate material, be it natural or synthetic. The filament 110 may be resorbable or otherwise. It may be a single-strand filament or a multi-strand filament, and it may be of any appropriate diameter.

The present invention applies particularly, but not exclusively, to a ligature filament provided with a sliding loop. More precisely, in the particular embodiment shown in FIG. 3, the filament 110 is provided at its proximal end 112 with a preformed loop 114 possessing a slip knot 116. The slip knot 116 may be of any appropriate type known to the person skilled in the art. It makes it possible to tighten the loop 114 by moving in translation along the main strand of the filament 110.

Figures 3, 9:
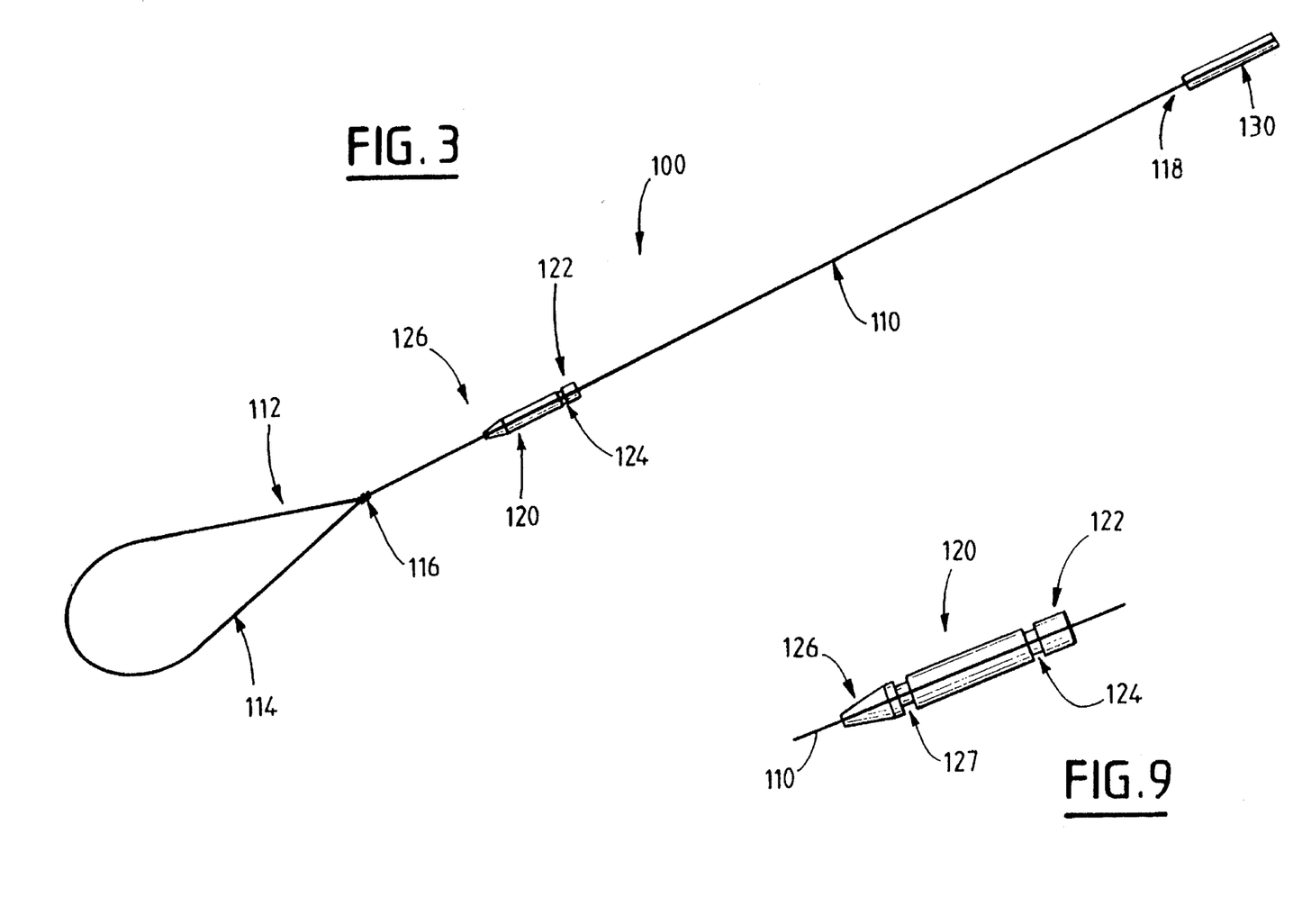
FIG. 3 is a diagrammatic view of a tie in accordance with the present invention.
FIG. 9 shows a variant embodiment of an endpiece in accordance with the present invention.

The tubular endpiece 120 is provided with a through longitudinal channel. The filament 110 is engaged to slide freely in the channel through the endpiece 120. As a result the filament 110 emerges from both ends thereof.

The endpiece 120 is made of a sterilizable material, e.g. a suitable plastics material.

The endpiece 120 is adapted to be mounted on a complementary reception cradle provided on the support 200. The cradle is described in greater detail below.

To this end, the endpiece 120 is provided with any appropriate means to enable said endpiece 120 to be secured on said support 200.

In the preferred embodiment as shown in FIG. 3, the endpiece 120 is made up of a cylindrical sheath of substantially constant outside diameter. Close to its distal end 122, the endpiece 120 is provided with an annular groove 124 going around its outside periphery. The groove preferably has a right cross-section that is of rectangular outline.

In addition, at its proximal end 126, the endpiece 120 preferably tapers. Thus, the proximal end 126 of the endpiece 120 is advantageously frustoconical. This disposition facilitates approaching an organ to ligate or suture without risk of causing trauma thereto.

The diameter of the internal longitudinal channel through the endpiece 120 must be greater than the diameter of the filament 110, while being less than the transverse size of the knot 116 to ensure that the knot cannot penetrate into the longitudinal channel through the endpiece 120, thereby enabling it to act as a knot-pusher relative to the knot 116.

The filament 110 is preferably also provided in the vicinity of its distal end 118 with an auxiliary endpiece 130.

Such an auxiliary endpiece 130 is used for recognition purposes and also for grasping purposes to apply direct manual traction on the distal end 118 of the filament 110 in order to facilitate ligating operations. The auxiliary endpiece 130 thus makes it possible to perform a complete manipulation blind, i.e. without visual observation of the filament (e.g. in the dark), and in particular without being able to see its distal end 118.

In addition, the auxiliary endpiece 130 has a right cross-section that is greater than that of the channel formed through the endpiece 120. The auxiliary endpiece 130 thus makes it possible to guarantee that the distal end 118 does not escape by passing through the endpiece 120.

Finally, as described below, the auxiliary endpiece 130 may constitute a cursor adapted to be slidably mounted on the handle 210 of the support 200, or else it may be adapted to be selectively mounted on such a cursor that is bonded permanently to the handle 210.

The auxiliary endpiece 130 is also made of a sterilizable material, e.g. a plastics material. The auxiliary endpiece 130 is bonded to the distal end 118 of the filament by any appropriate means, e.g. by stamping or by crimping.

The auxiliary endpiece 130 may be implemented in numerous different ways.

In the particular embodiment shown in FIG. 3, the auxiliary endpiece 130 is in the form of a cylindrical sleeve of constant outside diameter.

As explained below, particularly with reference to FIGS. 6 to 8, the auxiliary endpiece 130 may be shaped as a cursor adapted to be slidably mounted on the support 200.

The tie constituted by the filament 110, the main endpiece 120, and where appropriate the auxiliary endpiece 130, is packaged on a unitary basis, under ordinary conditions for sterile packaging. Such packaging is conventional in the field of ligatures and sutures and is not shown in the accompanying figures in order to simplify them, and it is not described in greater detail below.

However, it should be observed that packaging the tie 100 in this way makes it possible to reduce storage volume very considerably relative to that required for the known knot-pusher shown in FIGS. 1 and 2, and this constitutes a major advantage.

Figure 4:
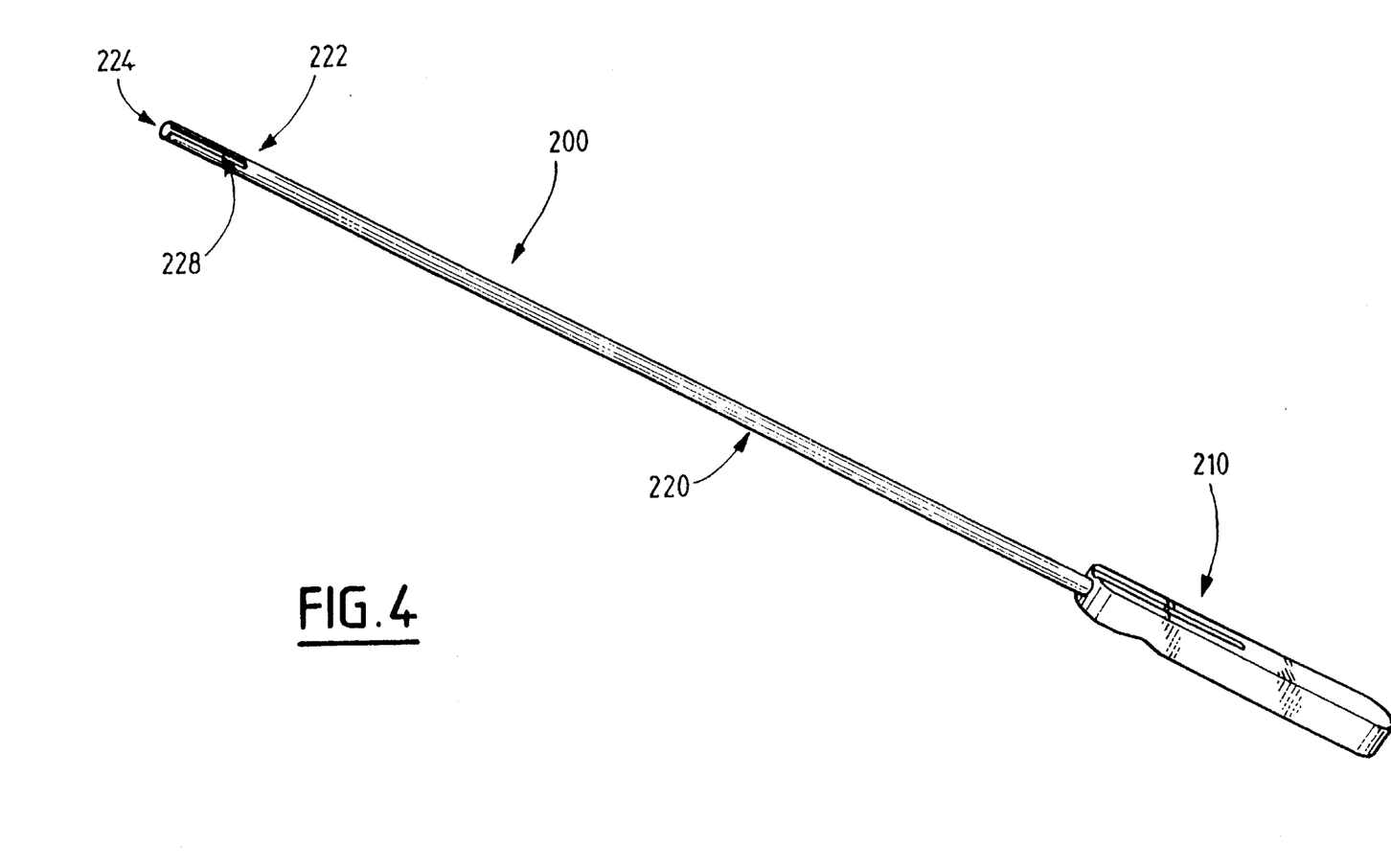
FIG. 4 is a diagrammatic perspective view of a support in accordance with the present invention.

The support 200 in accordance with the present invention essentially comprises a one-piece member comprising a handle 210 and a rod 220.

Here again, the support 200 is advantageously made of a sterilizable material. For example, the support 200 may be made of a metal, e.g. a metal based on stainless stele, or else it may be made of a plastics material.

Where appropriate, the support 200 may be formed by assembling together elements of different materials, for example by assembling together a handle 210 of plastics material and a metal rod 220.

The handle 210 may be implemented in numerous different ways with respect to its shape and/or its size. Numerous surgical instruments are already provided with handles that could be used in the context of the present invention. The handle depicted in this respect in the accompanying figures must therefore not be considered as being limiting. It is merely recalled that the handle 210 preferably has an outside surface that is not smooth and that does not constitute a circularly symmetrical body, thereby facilitating handling thereof.

The rod 220 is preferably rectilinear. It is provided at its proximal end 220 with a cradle 224 suitable for removably receiving the main endpiece 120 of the tie 100.

The reception cradle 224 may also be implemented in numerous different ways.

As shown in the accompanying figures, the reception cradle 224 is preferably formed by a central channel that opens out to the proximal axial end of the rod 220.

The axial channel 224 is preferably blind so as to facilitate operations of cleaning and of sterilization.

The inside diameter of the channel 224 used as the reception cradle must be adapted to the outside diameter of the endpiece 120.

In addition, the reception cradle 224 is provided with an appropriate retaining means, enabling the endpiece 120 to be removably secured to the proximal end of the rod 220.

Figure 5:
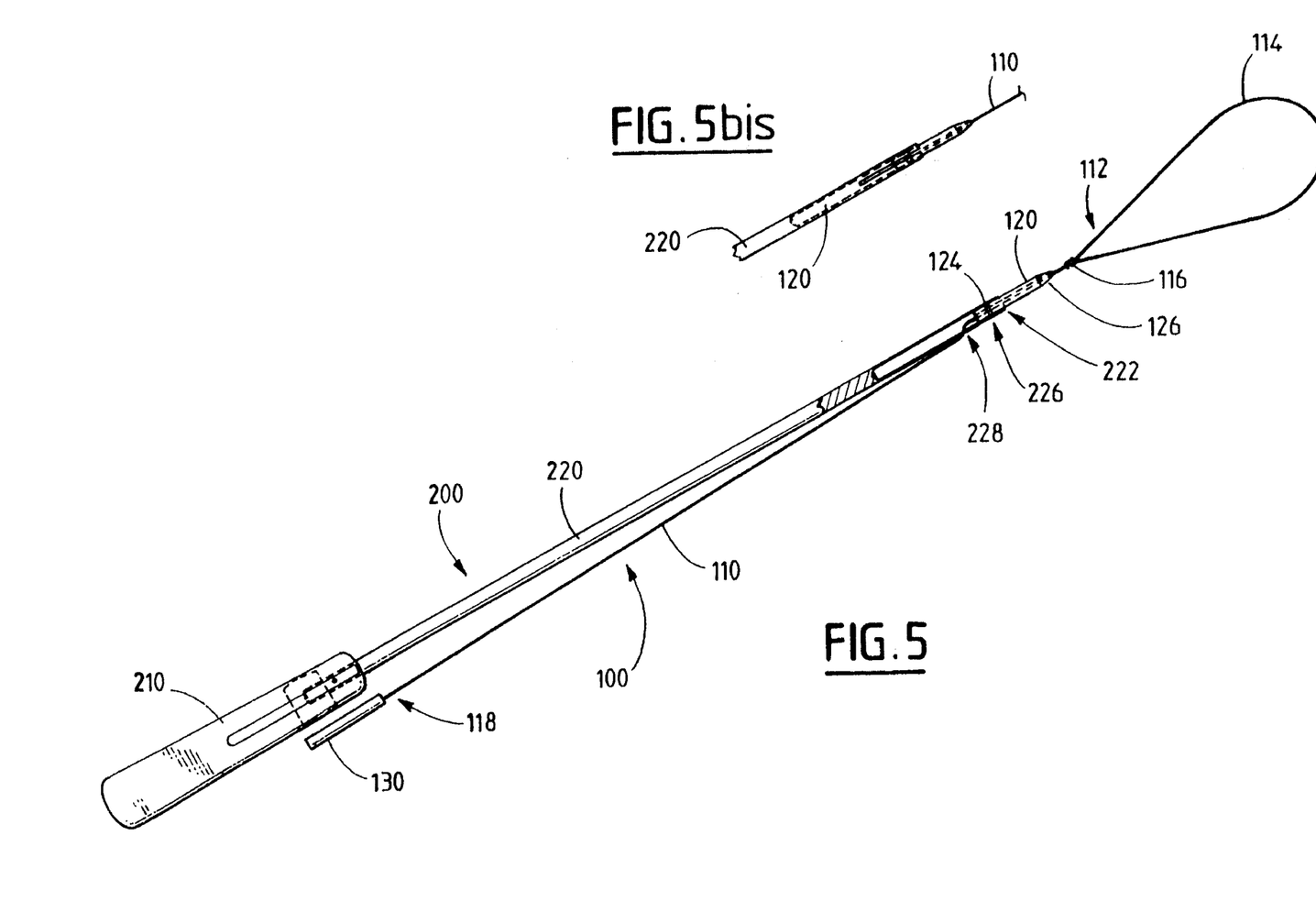
FIG. 5 is a diagrammatic view of the system of the present invention combining the tie and the support, with the support being shown in a view that is partially in longitudinal section.

In the preferred embodiment shown in the accompanying figures, and as visible in particular in FIGS. 5 and 5bis, the rod 220 is provided for this purpose at its proximal end, i.e. adjacent to the cradle 224, with an internal rib 226 that is complementary in size and in axial positioning to the groove 124 formed on the endpiece 120.

Naturally, the inverse disposition could be provided, i.e. it would be possible to provide a rib projecting from the outside periphery of the endpiece 120 and to provide a complementary internal groove in the cradle 224 of the rod 220.

In addition, in accordance with the invention, a through lateral window 228 is provided at the proximal end of the rod 220 through which said cradle 224 is accessible from outside the support rod 220. The window 228 is preferably rectilinear and parallel to the longitudinal axis of the rod 220.

The window 228 extends at least over the distal end of the cradle 224, i.e. the bottom thereof. However, as shown in FIG. 4, the window 228 may extend over the entire length of said cradle 224.

Because of the presence of the lateral window 228, the strand of filament 110 emerges from the distal end of the endpiece 120 can be disengaged on the outside of the rod 220 when the endpiece 120 is placed on the cradle 224, as can be seen in particular by examining FIGS. 5 and 5bis.

It will also be understood that the existence of a window 228 extending over the entire length of the cradle 224 makes it possible to increase the resilience thereof, and consequently to facilitate installation and removal of the endpiece 120.

The support 200 is preferably packaged separately from the tie 100. In addition, whereas the tie 100 described with reference to FIG. 3 is intended for use once only, the support 200 formed by the handle 210 and the rod 220 is preferably reusable. To this end, the support 200 must naturally be sterilized prior to each use thereof.

The system of the invention as described above is used and operated essentially as follows When the surgeon desires to make a ligature, it is necessary firstly to select an appropriate tie 100 as a function of the nature of the filament, and of its dimensions, and to extract the tie 100 from its sterile package.

The endpiece 120 of the tie 100 is then positioned on the proximal end of a support rod 220, i.e. at the cradle 224. While doing this, it is appropriate to see that the strand of the filament 110 emerging from the distal end of the endpiece 120 passes through the lateral window 228.

In this state, the loop 114 may be engaged in a trocar for operative purposes by inserting the proximal end 222 of the support rod 220 in said trocar.

Once the organ to be ligated has been placed inside the loop 114, it suffices to pull on the distal end 118 of the filament 110 relative to the support 200 in order to tighten the loop 114 about the organ to be ligated.

While that is taking place, it will be understood that the main endpiece 124 acts as a knot-pusher.

Naturally, the outside diameter of the support rod 220 must be less than the inside diameter of the longitudinal channel through the associated trocar.

In a particular embodiment given by way of nonlimiting example, the system has the following dimensional characteristics:

length of the endpiece 120: 30 mm;

diameter of the endpiece: 4 mm;

diameter of the internal longitudinal channel through the endpiece 120: 0.75 mm;

groove 124 situated 4 mm from the distal end 122 of the endpiece 120;

width of the groove 124: 1.5 mm;

depth of the groove 124: 0.25 mm;

width of the proximal tapering portion 126 of the endpiece 120: 7 mm;

length of the auxiliary endpiece 130: about 15 mm;

diameter of the auxiliary endpiece 130: 4 mm;

length of the support rod: about 330 mm; and outside diameter of the support 220: 5 mm.

Figure 6:
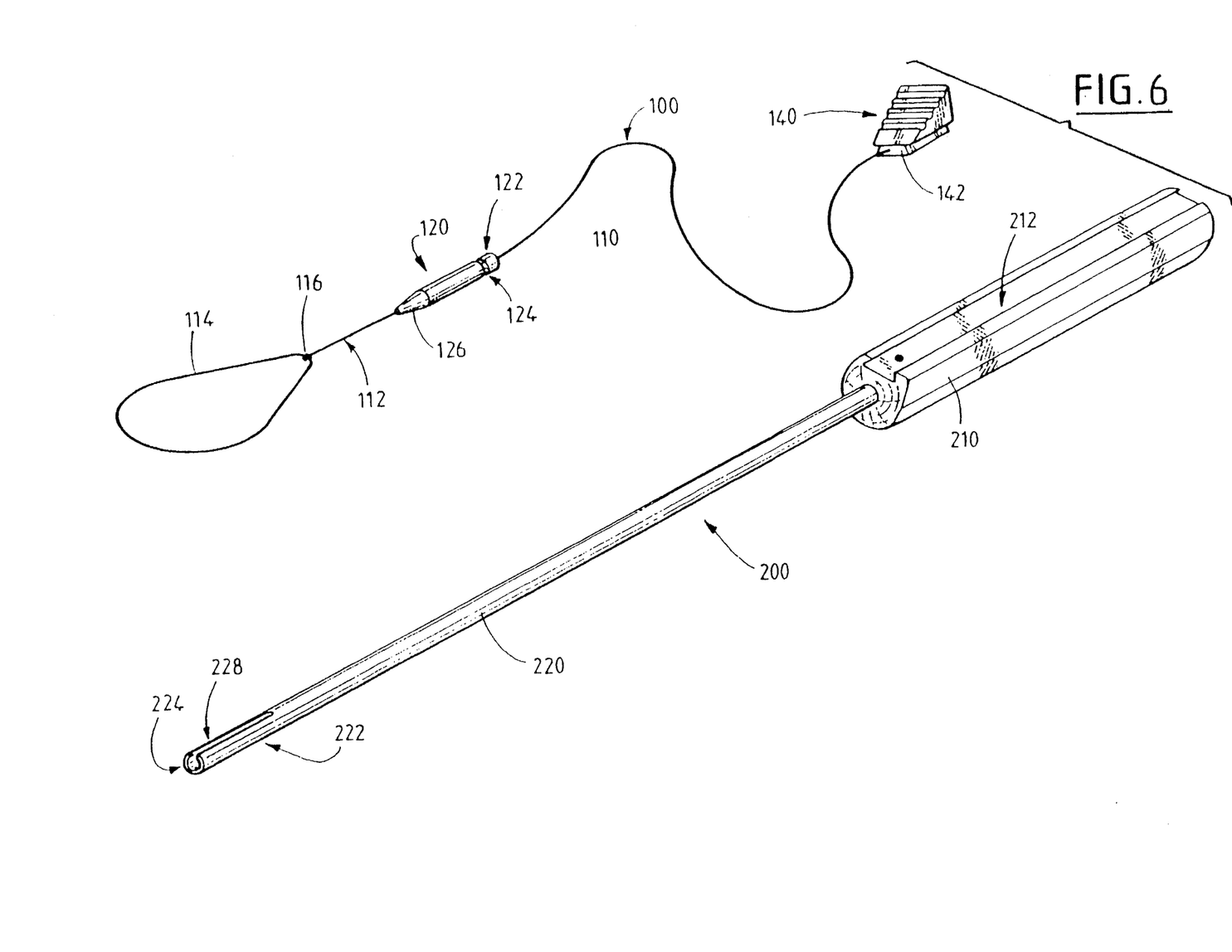
FIG. 6 is an exploded view of a variant embodiment of the system of the present invention, comprising a combination of a tie and of a support.

Accompanying FIG. 6 shows a variant embodiment in which the auxiliary endpiece 130 provided at the distal end 118 of the filament 110 is replaced by a cursor 140. The cursor 140 is adapted to be engaged in a complementary slideway 212 provided in the handle 210 of the support 200. The slideway 212 preferably extends in a direction that is generally parallel to the support axis. The slideway 212 is thus designed to guide the cursor 140 in axial translation and to facilitate tightening the loop 114 on the organ to be ligated.

The slideway 212 and the complementary cursor 140 may naturally be implemented in numerous different ways.

In the preferred embodiment of the present invention, the slideway 212 is constituted by a groove having convergent sides, e.g. in a dovetail configuration. The cursor 140 has a tenon 142 of right cross-section that is complementary to that of said slideway 212.

Naturally, in a variant, a longitudinal tenon could be provided on the handle 210 and a complementary groove could be provided in the cursor 140.

The use of such a cursor 140 guided in translation on the handle 210 instead of a simple auxiliary endpiece 130 as shown in FIG. 3 makes it possible to simplify handling of the system during a surgical operation. Whereas the embodiment shown in FIGS. 3 to 5 requires two free hands: one holding the support 200 and the other pulling on the auxiliary endpiece 130; the use of a cursor 140 as shown in FIG. 6 makes it possible to manipulate the system and to tighten the loop 114 by using one hand only. The surgeon can easily hold the handle 210 in one hand and displace the cursor 140 therealong by means of a finger of that hand, e.g. the thumb.

In the embodiment shown in FIG. 6, the cursor 140 forms an integral portion of the tie 100. It is fixed to the proximal end 118 of the filament 110. Consequently, the cursor 140 is packaged in the same sterile packaging as the tie 110 and the main endpiece 120.

Naturally, once the ligature has been completed, the cursor 140 together with the main endpiece 120 are discarded when excess filament is cut off.

Figure 7:
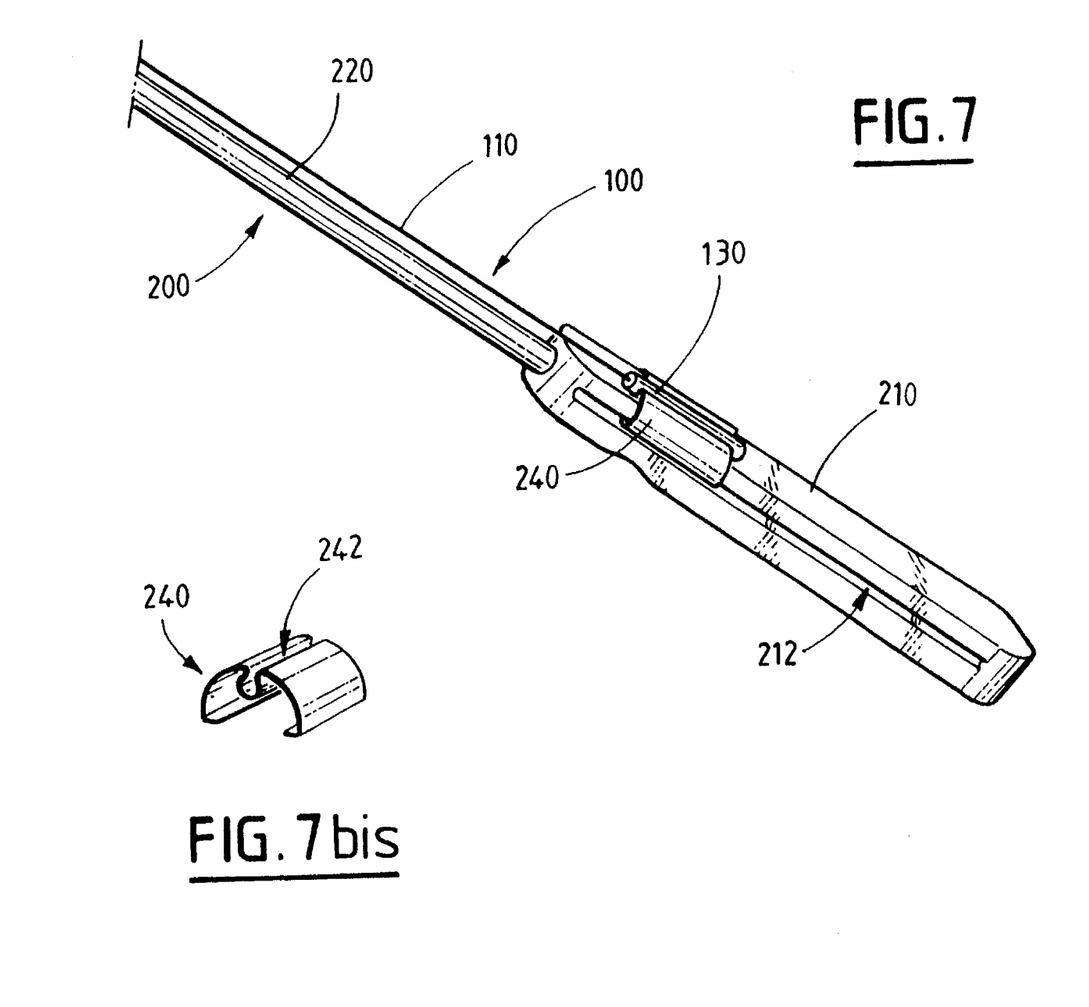
FIG. 7 is a view of the handle of a support constituting another embodiment of the present invention.

Accompanying FIG. 7 shows another variant embodiment in which a cursor 240 is provided that is reusable, the cursor being mounted for longitudinal sliding on the handle 210 and being adapted to receive the auxiliary endpiece 130 tied to the filament 110 and as shown in FIG. 3.

To this end, the cursor 240 comprises a clip 242 that is complementary to said auxiliary endpiece 130. Such a cursor 240 can be made of any appropriate material, e.g. by molding a piece of plastics material, or by folding a sheet of metal, e.g. stainless steel.

Where appropriate, provision may be made for the cursor 240 to be used once only. However, it is preferable for the cursor 240 to be adapted to receive the auxiliary endpiece 130 and to be permanently installed on the handle 210, which handle is preferably designed to be easily cleaned and sterilized.

The above embodiments all relate to so-called "endoloop" type devices, i.e. systems that include a slip knot loop 114 that is preformed prior to packaging on the proximal end of the filament 110.

Figure 8:
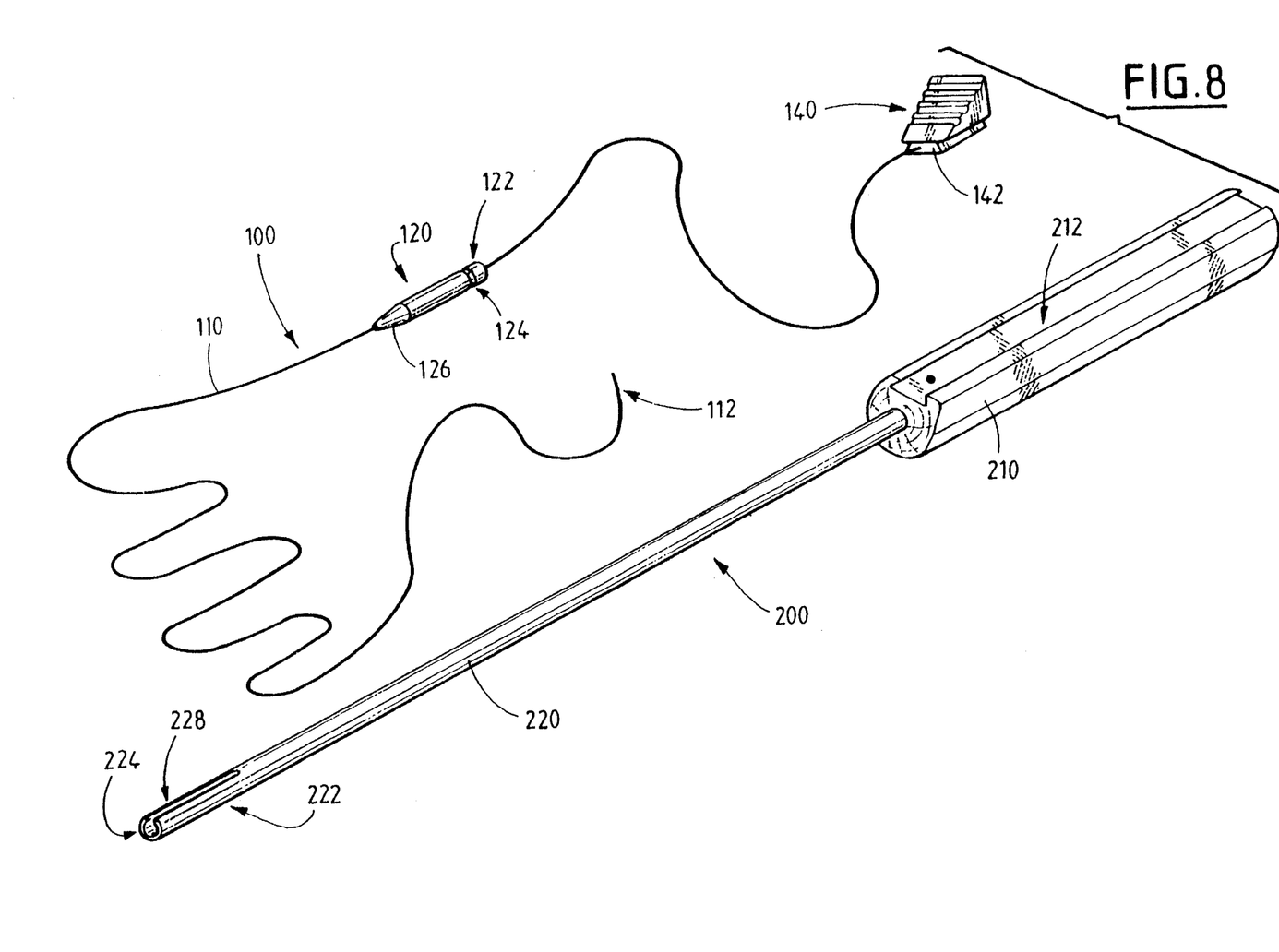
FIG. 8 shows a variant embodiment of the invention relating to a ligature.

However, as shown diagrammatically in FIG. 8, the present invention is not limited to that particular disposition, and it applies likewise to ties 110 that are not provided with such a preformed loop 114. The tie may be constituted by a single filament for endoligature with knots being tied inside or outside the body, and for which the endpiece 120 placed on the support rod 220 serves as a knot-pusher.

In the context of sutures, the filament 110 may be provided at its proximal end with a needle of any suitable shape, and in that case lock knots are made either inside the body or outside the body.

The system of the present invention offers the following advantages in particular:

it enables filaments 110 for ligature and/or suture and fitted with the endpiece 120 and optionally with the auxiliary endpiece 130 or with a cursor 140 to be stored compactly; it simplifies the operations of sterilization and of packaging;

handling is made possible using one hand only.

Naturally, the present invention is not limited to the particular embodiments described above, but extends to any variant coming within the spirit thereof.

Thus, for example, it is easy to adapt a cursor 240 that is permanently secured to the handle 210 as shown in FIG. 7 to receive an overhand knot or the equivalent formed on the distal end of the filament 110 in order to exert traction thereon merely by displacing the cursor 240.

It should be observed that the use of a tie engaged in a tubular endpiece, as required by the present invention, makes it possible to avoid the phenomenon of twisting as encountered using a laterally grooved or forked knot-pusher. Because of the invention, one of the filaments lies on the thrust axis. In addition, the single-use endpiece can be fitted accurately to the filament used, which is not true of multiple-use lateral groove or fork knot-pushers.

It is also possible to use the tubular endpiece 120 of the present invention (which is for use on one occasion only) as a filament passing system.

This may be advantageous when it is necessary to pass the filament around a structure that is relatively voluminous, such as the digestive tube or a large vessel, since the endpiece can facilitate identification of the filament located in depth around the rectum (for example) when it is desired to close it off by means of a loop.

To use the endpiece 120 as a filament-passing tool, it is possible, for example, to disconnect said endpiece 120 from the rigid support 200 and to manipulate the endpiece 120 by means of conventional forceps.

To facilitate reengaging the endpiece 120 on a support 200 after going round the structure, it is advantageous to provide a second annular groove on the endpiece 120 close to its proximal end 126, as shown in FIG. 9. This second groove 127 that is similar to the above-described groove 124 thus makes it possible to engage the proximal end 126 of the endpiece 120 in the cradle 224 of the rigid support 200, and to hold the endpiece 120 on the support 200 by co-operation between the groove 127 and the rib 226.

To facilitate manipulating the endpiece 120, it is also possible to provide a support 200 that possesses a cradle 224 whose longitudinal axis is inclined relative to the axis of the support 200, or a cradle 224 that is hinged on the proximal end 222 of the support 200 and that is associated with means that are controllable from the handle 210 for adjusting its orientation.

Such controlled hinge means are known to the person skilled in the art in the field of instruments for endoscopic surgery. There is therefore no need to describe them in detail herein.

Figure 10:
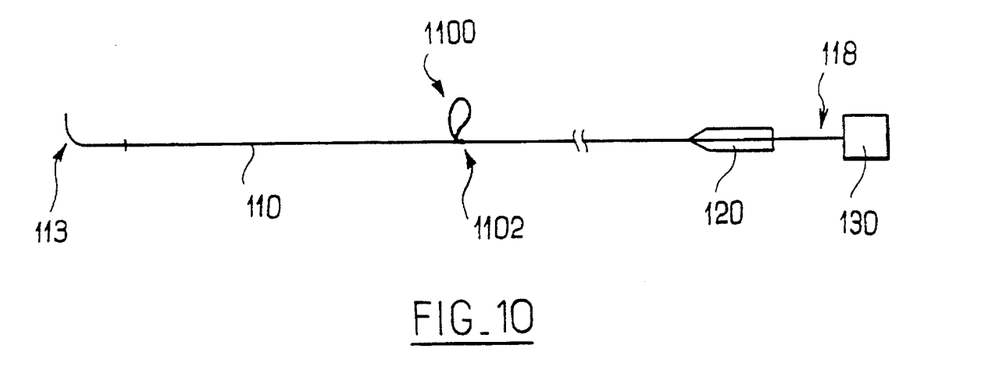
FIG. 10 shows a variant embodiment of a tie in accordance with the present invention.

FIG. 10 shows a variant embodiment of a suture in accordance with the present invention that includes a preformed loop 1100.

More precisely, in FIG. 10, there can be seen a tie in accordance with the present invention comprising a filament 110 provided with a needle 113 that is engaged in a tubular endpiece 120 and that is provided at its distal end 118 with an auxiliary endpiece 130. The filament 110 is provided beyond the endpiece 120, i.e. between the needle 113 and said endpiece 120, with a loop 1100 closed by a slip knot 1102. This tie makes it possible to simplify implementing a ligature since it suffices to pass the needle 113 through the preformed loop 1100 in order to obtain a ligature loop around an organ to be ligated, which ligature loop can be locked by closing the preformed loop 110 by applying traction to the proximal auxiliary endpiece 130.

Figure 11:
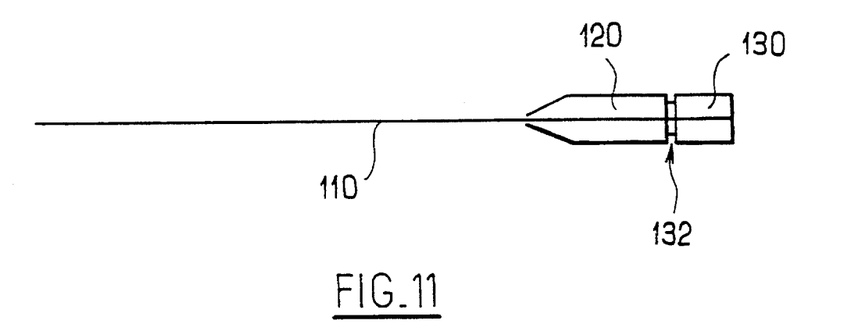
FIG. 11 shows anther variant embodiment comprising a tubular endpiece that is temporarily secured to an auxiliary endpiece.

FIG. 11 shows a variant embodiment of the tie that comprises a tubular endpiece 120 and an auxiliary endpiece 130 which are made by molding and which are initially united, i.e. prior to use they are united via a smaller-diameter zone of weakness 132 that is easily broken. This variant shown in FIG. 11 can be applied to all ties whether they are ligature or sutures, and in particular it can be applied to endoloop ties of the kind shown in FIG. 3, to endoligatures having knots made inside or outside the body, to ties using a needle, or indeed to ties including a preformed loop of the type shown in FIG. 10.

Figure 12:
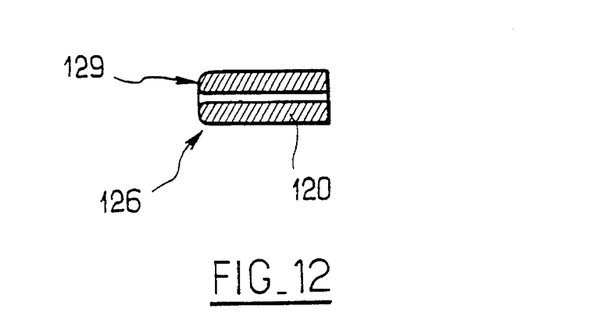
FIG. 12 is a longitudinal section view through an endpiece in accordance with the present invention.

FIG. 12 shows a variant tubular endpiece 120. In FIG. 12, the proximal end 126 of the endpiece 120 is no longer conical but is in the form of half a torus 129 centered about the central channel of the endpiece 120. This half-torus shape makes it easier to offset the two strands of the tie filament 110 and facilitates sliding of knots for locking purposes, in particular when the knots are implemented in the form of half-hitches in conventional manner for surgery.

Endoloop versions of the system of the present invention as shown in FIG. 3 make it possible to enlarge the size of a loop as much as is required, unlike the system in above-mentioned document WO-92/11810.

In the context of the invention it is important to use an endpiece 120 of plastics material and a support 200 that is perfectly rigid. The rigidity of the support makes it easier to push knots than in documents EP-A-0 477 020 and DE-U-9 204 296 as mentioned above which teach the use of supports that are plastic. In addition, the endpiece made of plastics material facilitates sliding of the tie 110.

Because it is possible to separate the endpiece 120 from the support 200, the invention makes it possible to implement a plurality of independent ligatures using different ties but by means of a single support 200.

It should also be observed that all prior art systems give rise to shear on the organ to be ligated while the loop of the ligature is being tightened. In contrast, the present invention makes it possible to avoid such shear because of the possibility of sliding the lock knot, in particular when it is in the form of a half-hitch, the knot then being slid along the strand on which the knot is formed and simultaneously sliding along the other strand so that both strands remain of substantially the same length.

Finally, the present invention makes it possible to implement all conventional ligature or suture techniques, including all types of knot known to the person skilled in the art, whether knotting is performed inside the body or outside it.

The present invention also makes it possible to provide a tubular thrust endpiece 120 that is well adapted to the size of the filament 110, and consequently to make knots that are well adapted to said filament.

In addition, the present invention makes it possible, should that be necessary, to interrupt the making of a ligature, to temporarily withdraw the tubular endpiece 120 of the support 200 while keeping the auxiliary endpiece 130 accessible outside the body for subsequently retrieving the ligature. The trocar released in this way can then be used for some other intervention. For example, if a hemorrhage problem occurs while making a ligature, it is possible to disconnect the endpiece 120 associated with the ligature from the support 200 while taking care that the corresponding auxiliary endpiece remains outside the body. The trocar is thus released. The endpiece 120 of a second appropriate tie can be placed on the support 200 and the second tie can thus be engaged via the trocar to perform hemostasis. Once that has been done, the second endpiece 120 is released and the first endpiece 120 is replaced on the support to finish off the ligature. Because of the structure of the invention all such interventions can be performed while using a single trocar. No prior art device offers that feature.

We claim:

1. A ligature and/or suture system for endoscopic surgery, comprising, in combination:

a length of suture having proximal and distal ends slidably mounted in the longitudinal channel of a separate tubular endpiece; and a rigid support including a handle secured to an elongate rod which is provided at its distal end remote from the handle with a reception cradle suitable for removably receiving the tubular endpiece, and with a through lateral window, whereby said cradle is placed on the outer surface of said support to enable the suture to pass therethrough and said support configured such that traction exerted on the proximal end of the suture by said support serves to tighten the suture.

2. A system according to claim 1 further including a cursor secured to said suture proximal end, wherein the handle of the support is provided with a slideway suitable for receiving said cursor.

3. A system according to claim 2, wherein the cursor is permanently secured to the proximal end of the tie.

4. A system according to claim 2, wherein the cursor is permanently mounted on the handle, which cursor is adapted to receive the distal end of the tie in removable manner.

5. A system according to claim 4, wherein the cursor contains a clip structure engageable with the slideway of said handle.

6. A system according to claim 2, wherein the slideway includes a groove having converging edges and the cursor has a tenon having complementary right cross-sections.

7. A system according to claim 1, wherein the tubular endpiece is made of plastics material.

8. A system according to claim 1, further comprising retaining means contained on the tubular endpiece for receiving said cradle thereon.

9. A system according to claim 8, wherein the retaining means comprise at least one annular groove formed on the tubular endpiece.

10. A system according to claim 8 wherein the retaining means comprise a rib formed on the inside surface of the reception cradle.

11. A system according to claim 8 further comprising distal and proximal ends on the tubular end piece wherein the retaining end means comprises two annular grooves formed on the tubular endpiece respectively in the vicinity of its proximal end and of its distal end.

12. A system according to claim 1, wherein the proximal end of the tubular endpiece is tapered.

13. A system according to claim 1, wherein the inside diameter of the longitudinal channel through the tubular endpiece is greater than the diameter of the filament constituting the suture while being less than the transverse size of a slip knot formed on said suture.

14. A system according to claim 1, wherein the reception cradle is formed by a longitudinal channel that opens out to the proximal axial end of the support rod.

15. A system according to claim 1, wherein the lateral window extends over the entire length of the reception cradle.

16. A system according to claim 1, wherein the suture is selected from the group comprising: a ligature filament provided at its proximal end with a preestablished loop having a slip knot; a simple ligature filament; and a suture filament provided with a needle at its proximal end.

17. A system according to claim 16, wherein the filament of the suture is provided with an auxiliary endpiece at its proximal end.

18. A system according to claim 17, wherein the auxiliary endpiece has a right cross-section that is greater than that of the channel passing through the tubular endpiece.

19. A system according to claim 17, wherein the auxiliary endpiece is adapted to be fixed on a cursor that is slidably mounted on the handle.

20. A system according to claim 1, wherein the suture comprises a preformed loop formed on the length thereof between its distal end and the tubular endpiece.

21. A system according to claim 1, wherein the proximal end of the tubular endpiece has a surface in the form of half of a torus.

* * * * *